United States Patent [19]

Psaras et al.

[11] 4,351,732
[45] Sep. 28, 1982

[54] DEHYDRATION OF ETHANOL

[75] Inventors: John D. Psaras, Arnold; James A. Zahniser, Severna Park, both of Md.

[73] Assignee: The C. M. Kemp Manufacturing Co., Glen Burnie, Md.

[21] Appl. No.: 215,738

[22] Filed: Dec. 12, 1980

[51] Int. Cl.³ ............... B01D 15/00; C07C 31/08
[52] U.S. Cl. .................................. 210/689; 55/33; 55/58; 55/62; 55/179; 55/208; 55/387; 208/310 R; 210/185; 210/274; 568/917
[58] Field of Search ............... 55/33, 35, 58, 62, 74, 55/179, 208, 387; 203/18, 19, 41; 208/310 R, 310 Z; 210/689, 274, 185; 568/916, 917

[56] References Cited

U.S. PATENT DOCUMENTS

| 1,661,149 | 2/1928 | Barnebey | 55/58 |
| 1,934,075 | 11/1933 | Lewis | 55/58 |
| 1,985,204 | 12/1934 | Derr et al. | 203/19 |
| 1,985,205 | 12/1934 | Derr | 203/19 X |
| 2,137,605 | 11/1938 | Derr | 203/41 X |
| 2,388,616 | 11/1945 | Lalande, Jr. | 210/689 |
| 2,472,912 | 6/1949 | McCarter | 210/689 |
| 3,037,338 | 6/1962 | Thomas | 55/58 |
| 3,085,379 | 4/1963 | Kiyonaga et al. | 55/58 X |
| 3,122,486 | 2/1964 | Skarstrom | 203/18 |
| 3,132,079 | 5/1964 | Epperly et al. | 203/41 |
| 3,161,488 | 12/1964 | Eastwood et al. | 210/689 X |
| 3,283,025 | 11/1966 | Lenz et al. | 208/310 R X |
| 3,421,984 | 1/1969 | Jensen et al. | 203/41 |
| 3,538,168 | 11/1970 | Mitchell, Jr. | 568/916 X |
| 4,273,621 | 6/1981 | Fornoff | 203/19 |
| 4,277,635 | 7/1981 | Oulman et al. | 568/917 X |

FOREIGN PATENT DOCUMENTS

| 2263995 | 10/1975 | France | 568/917 |
| 882946 | 11/1961 | United Kingdom | 568/917 |
| 240694 | 8/1969 | U.S.S.R. | 568/916 |
| 357218 | 1/1973 | U.S.S.R. | 568/917 |

Primary Examiner—Robert H. Spitzer
Attorney, Agent, or Firm—Fidelman, Wolffe & Waldron

[57] ABSTRACT

Process and apparatus for dehydrating liquid phase ethanol in an adsorber unit containing at least two towers that cycle between adsorption and desorption cycles, characterized in the desorption cycle by an indirect heating volatilization of absorbed and adsorbed liquid at ambient pressures, and by a final stages desorption under sub-atmospheric pressures. In preferred practice, an inert sweep gas at sub-atmospheric pressures assists in removal of vapors evolved in the final stages of the desorption cycle.

8 Claims, 6 Drawing Figures

BED TEMPERATURE DURING REGENERATION

4,351,732

DEHYDRATION OF ETHANOL

INTRODUCTION

This invention relates to ethanol dehydration system employing a pair of adsorbent beds arranged for alternatively shifting between cycles of adsorption and desorption.

RATIONALE OF THE INVENTION

In recent years the ever increasing value of fossil hydrocarbon liquids and gases has directed attention to the possibilities of employing bio-mass materials for fuel purposes. In particular, attention has been directed to the possibilities for employing fermentation derived ethanol alone or in a mixture with gasoline fraction hydrocarbons for automotive fuel purposes. The mixture of 90% hydrocarbon 10% ethanol is popularly known as gasohol.

However, for satisfactory storage the gasohol mixture should have essentially no water therein, or else phase separation occurs. In practice this means that ethanol employed for gasohol purposes must be at least 199 proof ethanol.

As is well known to the art, the ethanol water system forms a minimum boiling azeotrope at 190 proof i.e., 95% ethanol by volume. Accordingly, distillation recovery of ethanol from a fermentation mash proceeds no further than 190 proof. Special techniques are required to dehydrate ethanol beyond the 190 proof ethanol content level.

The present invention is directed to an adsorption system suited to dehydration of 190 proof ethanol to more than 199 proof ethanol.

BRIEF STATEMENT OF THE INVENTION

Briefly stated, the present invention relates to a process and an apparatus system for dehydration of ethanol which comprises two adsorbent or desiccant beds arranged for alternatively shifting between cycles of adsorption and desorption. Liquid phase ethanol is passed through the bed operating in the absorption portion of the cycle whereby the adsorbent adsorbs the water content of the ethanol so that an essentially anhydrous stream of ethanol i.e., at least 199 proof ethanol leaves the adsorption bed. During the desorption portion of the cycle the saturated desiccant bed is heated by an indirect heat exchange means immersed therein, to vaporize the adsorbed liquid. Inert gas is passed through the desiccant bed at least in the final stages of regeneration to sweep out the vaporized water and alcohol vapors, thereby regenerating the desiccant bed for renewed use during the adsorption portion of the cycle. Important to practice of this invention is employment of a sub-atmospheric pressure gas sweep in the final stages of the desorption (or regeneration) cycle. At the expiration of the desorption portion of the cycle heat exchange means immersed in the desiccant bed are employed to cool the desiccant back to the temperatures suited for adsorption.

The practice of the present invention employs operating conditions adapted to insure long life for the adsorbent material of the desiccant beds. Low energy utilization and reduced capital expense characterize the system of this invention.

DETAILED DESCRIPTION OF THE APPARATUS

For further understanding of the invention, reference is now made to the attached drawing wherein.

Figure 1:
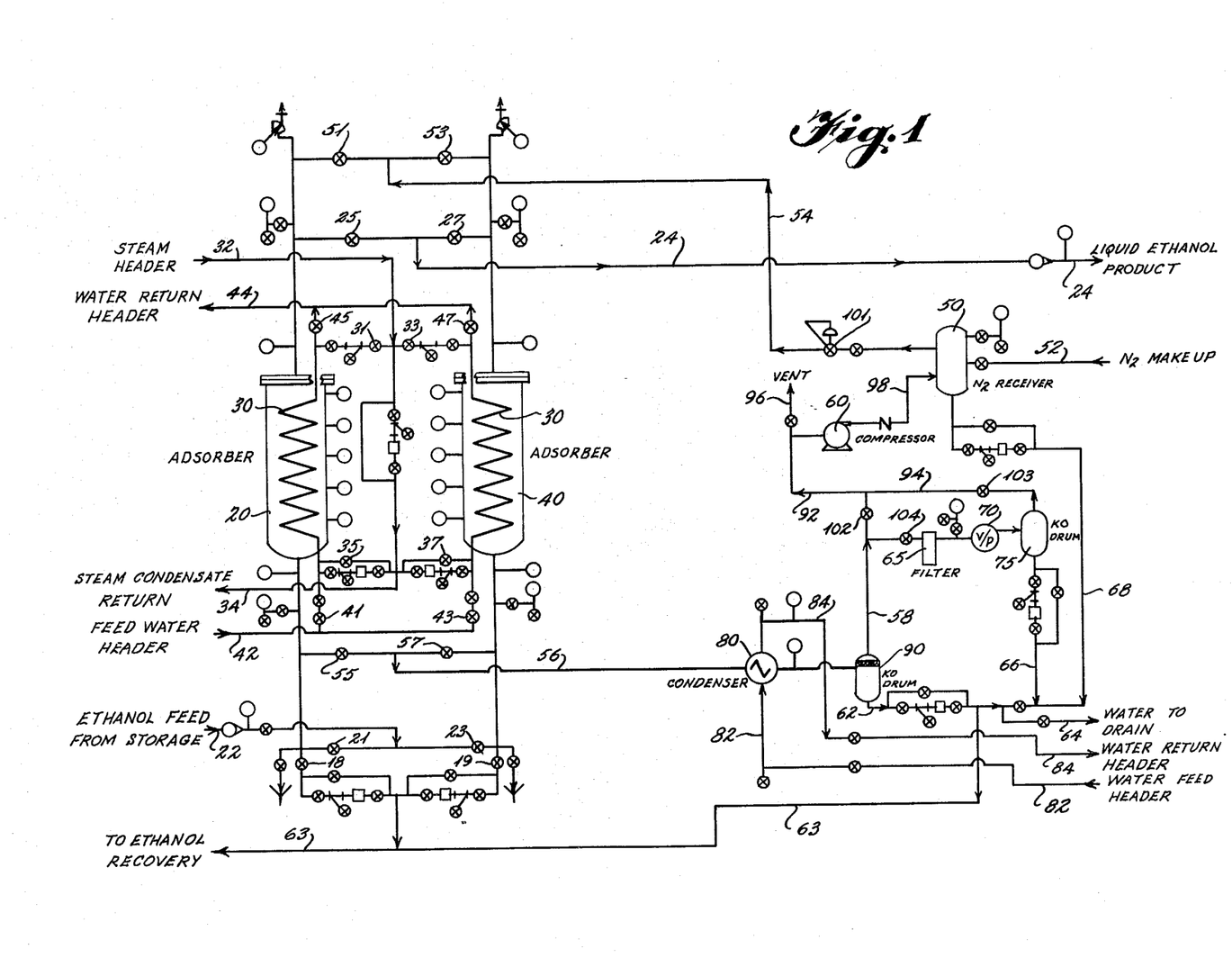
FIG. 1 is a flow sheet representation of the ethanol dehydration system of the present invention.

Referring now to FIG. 1 whereon is illustrated the ethanol dehydration system of this invention, it may be seen there that ethanol is dehydrated by passage through one or another of a pair of adsorber vessels 20 and 40 containing desiccant beds which beds suitably may be formed from particulate adsorbent. (Many desiccants are commercially available including, for example, alumina, silica gel and numerous zeolites and, therefore, the desiccant need not be described herein in detail.) Imbedded inside each of adsorber vessels 20 and 40 and inside the particulate desiccant bed therein, is a heat exchange coil 30. Steam from a steam header (not shown) e.g., 150 psig steam enters the ethanol dehydration system to pass by way of line 32 and one of the valves 31 and 33 appropriately to the steam coil 30 in either adsorber bed 20 or 40. The steam condensate passes from coil 30 by way of the valve 35 or 37, as appropriate, into a steam condensate line 34 to leave the dehydration system as the steam condensate return. When regeneration of a desiccant bed commences, the steam heats the bed inside adsorber vessel 20 or 40 to regeneration temperature levels, which levels exceed 212° F. and preferably are in the range of 325° F. to 375° F.; indirect heat exchange with the steam serves to vaporize the adsorbed materials, i.e., water, ethanol, fusel oil if present, etc.

As has already been indicated, heat exchanger means are also employed at the end of the regeneration cycle to cool the freshly regenerated bed of adsorbent to operating temperatures for adsorption. The drawing illustrates a mode using heat exchange coil 30 for this purpose. Thus, cooling water entering from a feed water header (not shown) passes into the system by way of line 42 and then through valve 41 or 43 as appropriate into the heat exchange coil 30 of adsorber bed 20 or 40. The heated water passes out of the heat exchanger 30 by way of valve 45 or 47 as appropriate into outlet line 44 from which the heated water passes to a water return header outside the dehydration system.

The liquid phase ethanol to be dehydrated, e.g., 190 proof ethanol, enters line 22 of the system from some suitable storage vessel (not shown), then passes by way of valve 21 or 23 as appropriate into the adsorber vessel 20 or 40 to flow directly through the bed of desiccant therein, and after being dehydrated by the desiccant leaves the adsorber by way of valve 25 or 27 to exit from the dehydration system through outlet line 24. The ethanol is dehydrated to more than 199 proof.

A low pressure inert gas, nitrogen for example, is employed in the dehydration system to sweep the evolving vapors from the adsorber bed undergoing regeneration. As can be seen in the drawing then, nitrogen or other inert gas is introduced into a gas recirculation loop from line 52. During operation of the dehydration system line 52 feeds nitrogen make-up to nitrogen receiver or holding tank 50, from which recirculating nitrogen is drawn in line 54 through a pressure reducing valve 101 to pass through either valve 51 or 53 as appropriate, into adsorber vessel 20 or 40 sweeping through the adsorber bed undergoing regeneration. The sweep gas i.e., nitrogen and vapors evolved from the desiccant bed leaves the adsorber vessel by way of valve 55 or 57 into line 56, then goes through a water cooled condenser 80.

Passage of the inert gas and vapors mixture through condenser 80 causes the vapors to condense to liquid phase; condensate is removed from the sweep gas stream at knockout drum 90. The condenser 80 is operated in the range of 35°-100° F. by coolant that enters the dehydration system from line 82 and leaves (warmed) through line 84, e.g., cooling water.

Figure 5:
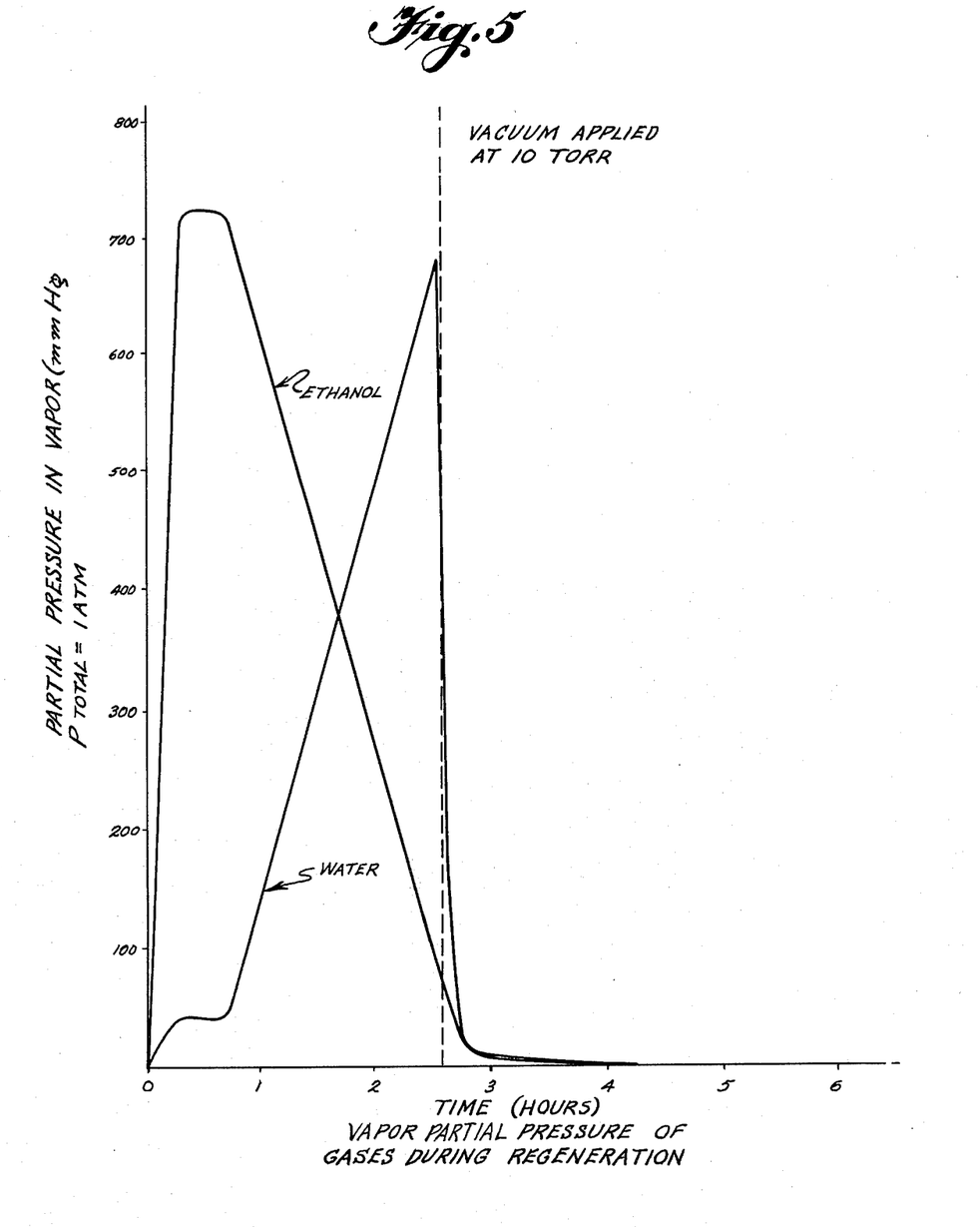
FIG. 5 is an idealized histogram of vapors taken off a desiccant bed that had been employed to dehydrate a pure ethanol-water azeotrope to more than 199 proof ethanol.

During the course of a regeneration cycle the vapors condensed at condenser 80 then separated from the inert gas sweep by knockout drum 90 and taken off in liquid phase by way of line 62 changes in composition, as is illustrated in FIG. 5. The forerunnings, which are the vapors removed from the desiccant bed of adsorber 20 or 40 at the beginning of the regeneration cycle are at about 190 proof and with time, the ethanol content of the condensate decreases. High alcohol content condensate is sent through line 63 back to an ethanol recovery arrangement that forms no part of this invention. Later on in the regeneration, the condensed vapors become largely water. Such condensed water vapors are passed to a drain line 64 for removal from the dehydration system.

The inert gas stream e.g., nitrogen from knockout drum 90 may pass by way of line 92 directly to compressor 60 and then through line 98 into the (nitrogen) gas storage tank 50 to complete the gas loop that goes from tank 50 back to tank 50.

Inasmuch as most gas loops have a tendency to accumulate undesired non-condensibles such as air that was dissolved or otherwise entrapped in the ethanol feed stream, a bleed vent 96 is provided on line 92.

Also shown in the flow sheet of FIG. 1 is the evacuation arrangement operated during regeneration of the desiccant wherein when valve 102 is closed and valves 104, 103 are opened, the gases taken from knockout drum 90 by way of line 58 pass through a filter 65 then a vacuum pump 70 thereafter second knockout drum 75 and then go by way of line 94 and line 92 to the compressor 60, and storage tank 50.

The additional knockout drum 75 and drain line 66 therefrom, as well as drain line 68 from the inert gas (nitrogen) receiver tank 50 remove water condensed out of the inert gas in the flow lines or in tank 50. The drain lines 66 and 68 feed into the water drain line 64 for disposal from the system. Presence of the additional drain lines is desirable inasmuch as flow of the inert sweep gas is variable; therefore, water vapor not condensed by condenser 80 may be condensed in the flow lines ahead of knockout drum 75 or in gas receiver tank 50 (particularly during cold weather).

FURTHER DISCUSSION OF THE INVENTION

Many of the individual features combined into the above described adsorptive dehydration of ethanol system of this invention have long been suggested to the art, as witness the teachings in U.S. Pat. No. 2,137,605 to indirectly heat and cool the adsorption beds. However, insofar as the inventors herein are aware, the art has not attempted to conduct an adsorptive dehydration of ethanol with the least possible consumption of thermal energy, and to minimize the capital expense of the equipment needed to carry out ethanol dehydration.

Thus, the patent 2,137,605 suggestion of dehydrating a vapor phase stream of ethanol is believed to be less advantageous than adsorption removal of water from a liquid phase stream of ethanol. In passing it may be noted that patent 2,137,605 expresses concern over thermal effects on the desiccant bed from heat generated by condensation of water (from the vapor) during adsorption. In applicants' system water is already in liquid phase and, therefore, a far lower molar enthalpic change takes place upon adsorption of the water by the desiccant i.e., no heat of condensation. In addition, liquid phase adsorption offers a substantial equipment advantage because mass transport rates for liquid phase materials are far greater than for gas phase materials (passing through the same size vessels and flow lines).

An ethanol dehydration system of which the inventors herein are aware dehydrates ethanol by passage of liquid phase ethanol through a twin tower desiccant bed system. However, this particular system regenerates the desiccant beds by flowing heated inert gas through the desiccant bed (undergoing regeneration). A large volume of gas must be recirculated in order to provide (through direct heat exchange) all the thermal energy required to heat the desiccant bed and to vaporize all the liquid absorbed and adsorbed thereon and appropriately large gas flow conduits are required for the gas loop. Regeneration through direct heat exchange suffers from other disadvantages as well.

The preferred embodiment of this invention retains the advantages of liquid phase adsorption and the advantages of a gas sweep that assists desorption of the vapors, while avoiding the disadvantages of a direct heat exchange by providing the heat of desorption from a heat exchanger disposed inside the desiccant bed, heating with steam for example. Later the desiccant bed is cooled (for renewed adsorption) through indirect heat exchange for example by passing cooling water through the same or separate heat exchanger. Low volume flow of sweep gas will suffice and correspondingly, flow lines, compressors, etc. are relatively small, minimizing thereby equipment expense.

Figure 2:
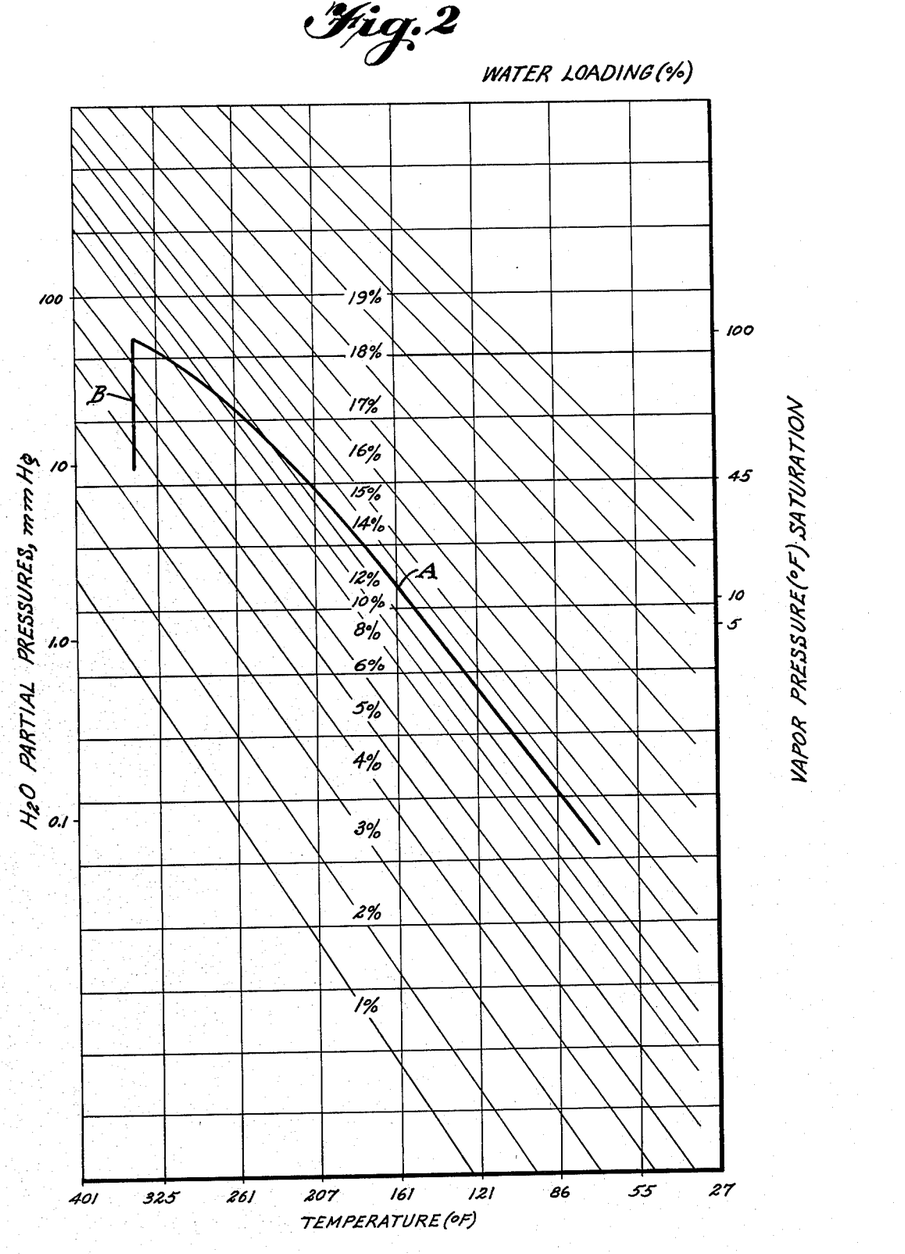
FIG. 2 is a graph of the equilibrium water content of a typical desiccant at different saturation vapor pressures and temperatures (% $H_2O$ v. F.°), illustrating the effect of sub-atmospheric gas pressure thereon.

One individual feature important to practice of this invention not known to be suggested in the art is employment of sub-atmospheric pressure for regenerating the desiccant, the reduced pressure being applied in the final stages of regeneration. The significance of this feature to practice of this invention can best be appreciated from review of FIG. 2 whereon is illustrated the water content equilibria of a typical commercial desiccant (Davidson, Union Carbide or LaPorte 3A° for example). Shown in FIG. 2 is the equilibrium water content levels of the typical desiccant at various temperatures in the presence of 100° F. dew point gas at atmospheric pressure. (100° F. is a dew point reasonably obtainable in condenser 80.)

It may be noted that the atmospheric pressure equilibrium varies with temperature, going from about 17% water content in the desiccant at 212° F. (100° C.) to about 7% at 350° F. Thus, during a commercial adsorption cycle carried at atmospheric pressure such a desiccant might well go from 7% water content to about 13% and regenerate from 13% to about 7% (ignoring for the moment that some of the adsorbed liquid would in fact be ethanol). Such a cycle is illustrated as Curve A on FIG. 2. If, however, the gas pressure on the 350° F. desiccant were reduced to 10 torr, the equilibrium water content of the desiccant drops to the 350° F. point on the equilibrium curve for the desiccant at 10 torr pressure in the presence of the same gas, (Curve B) namely to a water content in the desiccant of below about 4%. Thus, an adsorption/desorption system which includes completing the regeneration under sub-atmospheric pressure allows the desiccant to cycle from 4–13% water, increasing adsorption capacity substantially as compared to an atmospheric pressure regeneration with the same sweep gas.

As a practical matter some of the capacity improvement obtainable by sub-atmospheric pressure regeneration may be foregone in favor of economic factors such as capital equipment costs.

As is already clearly evident the operating conditions for both adsorption and desorption are important to practice of the present invention. Adsorption is carried out in adsorber vessels 20, 40 as a liquid phase operation at temperatures not exceeding the boiling point of the azeotrope (177° F.), in the range of ambient to boiling point. Desorption removal of absorbed and adsorbed water and ethanol i.e., all sorbed liquids is a gas phase operation at temperatures above the boiling point of the azeotrope, which during the initial desorption phase, if desired, by a relatively low pressure inert sweep gas passing through the desiccant bed, e.g., a pressure of 15 to 20 psia. Regeneration is then completed under sub-atmospheric pressure preferably aided by an inert gas sweep.

Under the rather mild temperature conditions herein contemplated the desiccant bed is never heated to a level where the particle surfaces thereof become catalytic to chemical reactions, such as, for example, decomposition of ethanol to ethylene, or polymerization of reactive components in fusel oil if such is present. The preferred regeneration temperature range of 325° F.–375° F., combined with vacuum creates a satisfactory useful water capacity or loading for commercially available desiccants.

OPERATION OF THE PROCESS

To facilitate understanding of the process, practice of this invention will hereafter be described in terms of the exemplary embodiment thereof illustrated in FIG. 1 of the drawing, which in a commercialized system would for example, be sized to dehydrate about 10 million gallons (per year) of 190 proof ethanol to at least 199 proof using about 63,000 pounds of desiccant in each of adsorber vessels 20 and 40. Ancillary instrumentation and valving for such size system are indicated on FIG. 1 but not legended.

The 190 proof ethanol at about 100° F. entering at line 22 is passed through one of the adsorber vessels, adsorber 20, for example, being dehydrated therein to more than 199 proof before leaving the system through line 24. After a predetermined adsorption period, e.g., 8 hours of ethanol flow, the desiccant bed in adsorber 20 has reached about a 15% water content (based on the dry bed weight) valves 21 and 25 are closed. Opening previously closed valves 23 and 27 brings adsorber 40 into service for the adsorption cycle, and commences the regeneration cycle for adsorber 20.

Then valves 51 and 18 are opened to pass nitrogen from nitrogen storage tank 50 at 15-20 psia by way of line 54 to adsorber 20 to force the liquid phase ethanol present in adsorber vessel 20 into reverse flow, draining out past (opened) valve 18 into ethanol recovery line 63. Valve 19 serves a like ethanol recovery function for draining adsorber 40. A liquid pump not shown may be used to assist draining. Moreover, if a pump is provided, the gas sweep may be omitted at this stage in the regeneration cycle.

After the liquid ethanol has been drained from adsorber vessel 20, valve 18 is closed and valve 55 is opened, to establish the sweep gas loop through condenser 80, knockout drum 90 and compressor 60 back into tank 50. Valves 104 and 103 are left closed, which keeps the vacuum pump 70 out of the gas loop. After draining is complete, the gas flow may be reduced to a trickle, or even stopped altogether by at an least partial closure of valve 101. In any event, after draining out the liquid ethanol the adsorber 20 is now at about atmospheric pressure ethanol e.g., 15-20 psia.

At this stage of the regeneration cycle desiccant bed contains water and ethanol adsorbed and absorbed. The bed water content is 15-20% of the dry bed weight, and the sponge ethanol remaining thereon is about 25-30% of the dry bed weight.

Figure 3:
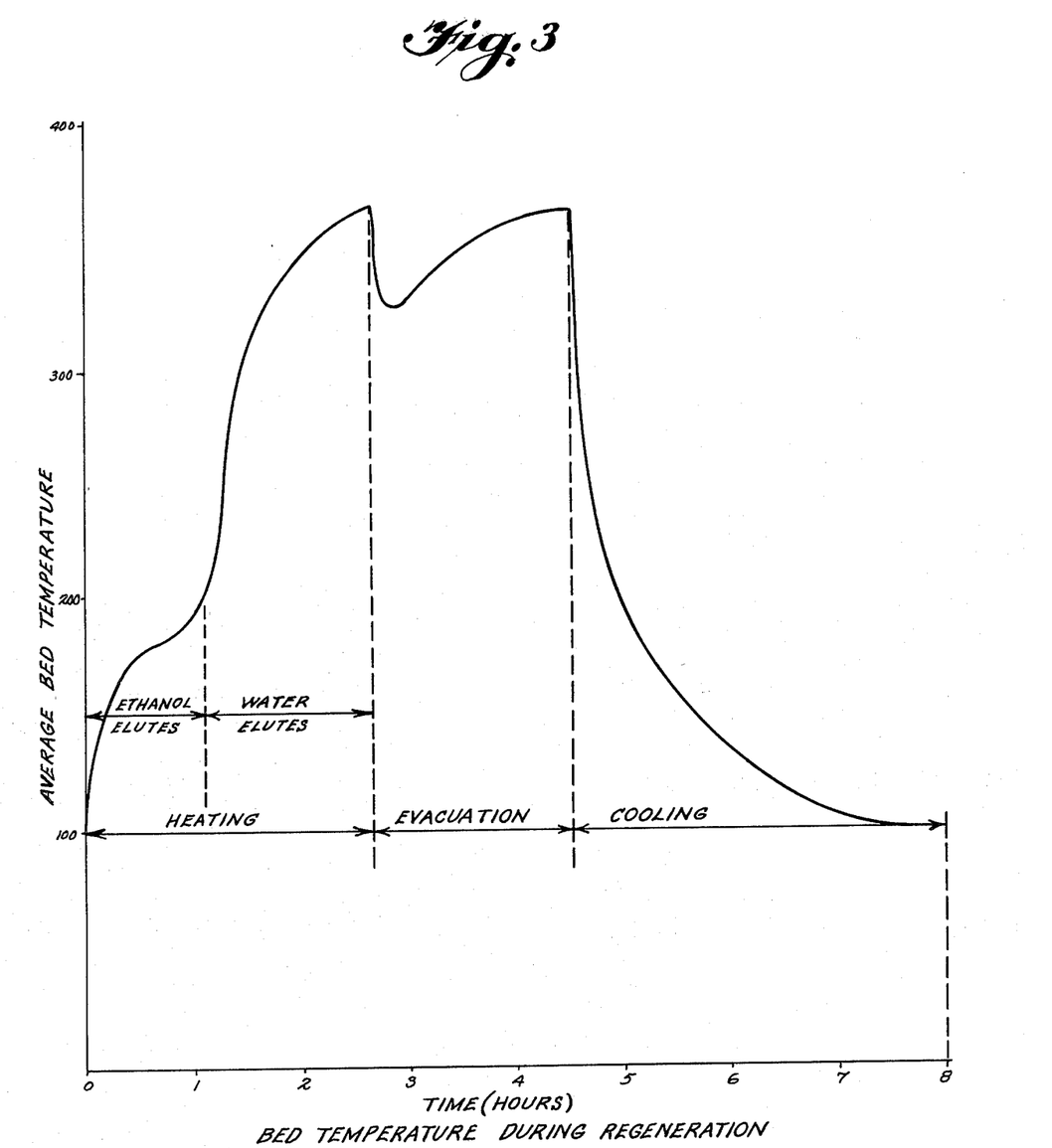
FIG. 3 is a graph of time v. temperature (F.°) for the adsorbent bed undergoing desorption.
Figure 4:
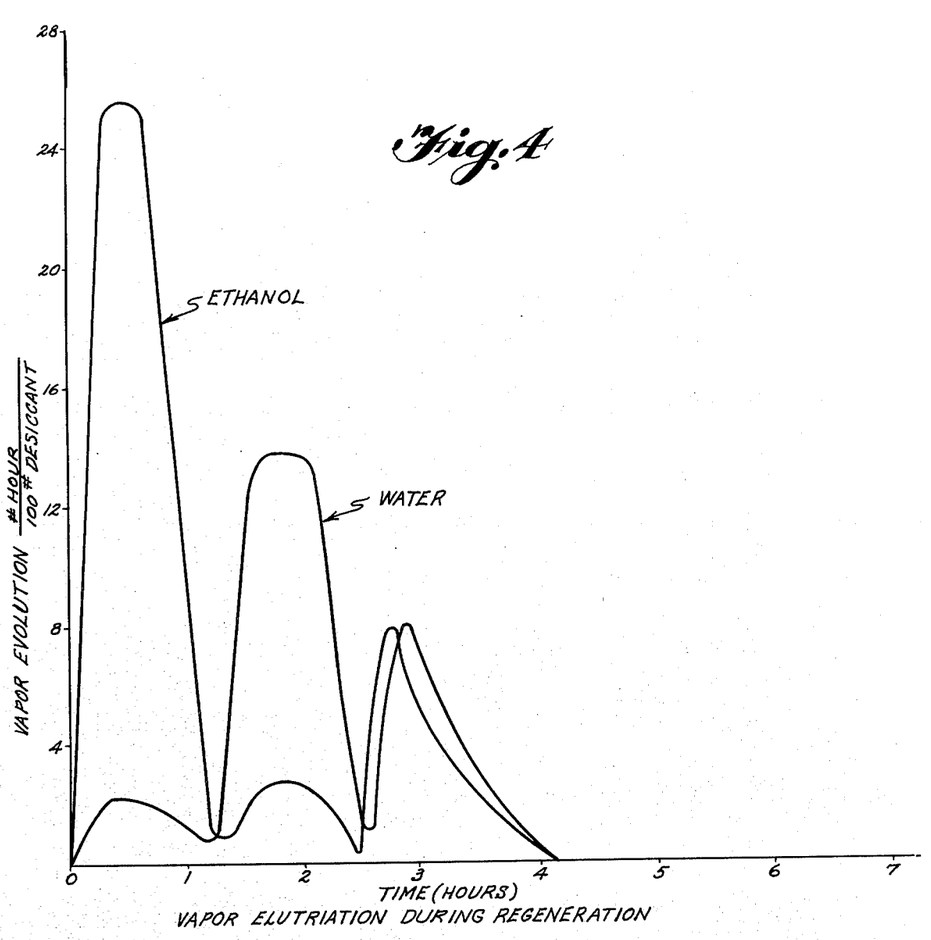
FIG. 4 is a graph of time v. vapor evolution rate for the adsorbent bed undergoing desorption.

Steam line valve 31 and steam condensate line valve 35 are then opened so steam (e.g., 150 psig steam) entering at line 32 passes through coil 30 to heat the bed and to vaporize absorbed and adsorbed water and ethanol, the steam condensate drains through line 34. FIG. 3 illustrates the rate at which bed heats up even as sponge and adsorbed vapors are evolved from the bed. FIG. 4 illustrates the rate at which the ethanol and water vapors evolve from the desiccant bed. FIG. 5 shows the partial pressure of ethanol and water in the elutriated vapors over the course of the regeneration.

As may be seen best on FIGS. 3 and 5, regeneration is first conducted under about atmospheric pressure conditions. During this, the main portion of the regeneration cycle, almost all of the sponge ethanol and most of the adsorbed water are vaporized, as is evident from FIG. 4. In an exemplary instance the main portion of the regeneration cycle lasts about 2½ hours. During this main portion of the regeneration cycle valve 101 may be closed, because passage of sweep gas would serve almost no function other than to prevent ethanol and water vapors from backing up into the gas line 54. The large volumes of vapors volatilized from bed 30 will themselves flow downstream by way of line 56 to condenser 80 and knockout drum 90.

The high vapor partial pressure present in the gases flowing through line 56 during this main portion of the regeneration cycle permits a conventional (surface) water cooled condenser 80, operating within a temperature range of 35°–100° F. to recover as condensate nearly all of the sponge alcohol. The condensate recovered by knockout drum 90 during the main portion of the regeneration cycle is passed to line 63 for flow to an ethanol recovery arrangement.

After the about 2½ hours of regeneration, most of the adsorbed and absorbed ethanol and water has been evolved from the bed of desiccant, i.e., the bed is near to the end point of Curve A on FIG. 2. The mean bed temperature has reached about 350° F. and the water content thereof is about 5% or 6% of the dry bed weight. Then vacuum pump 70 is placed on stream in the gas loop; valve 102 is closed, valves 103 and 104 are opened. In preferred practice of this invention, a sub-atmospheric inert gas sweep is employed. At this time then, valve 101 is set to allow a trickle of nitrogen. A reasonable size vacuum pump system (e.g., 80 hp) operating for about 2 hours will draw the pressure down to about 10 torr (about 10 mm hg) at condenser 80 operating with 35°-40° F. cooling water at which sub-atmospheric pressure the desiccant will dehydrate from about 5-6% water content to about 3-4% water content as is indicated by Curve B of FIG. 2. As can be seen on FIG. 4, applying vacuum sharply increases the vaporization rate, both for water and ethanol. The secondary or vacuum condition stage or portion of the regeneration cycle lasts for about 2 hours.

Thereafter steam line valve 31, and the steam condensate return valve 35 are closed, then water line valves 41 and 45 are opened. Vacuum pump 70 is halted; valves 103, 104 are closed; valve 102 is opened. Valve 101 may be cracked open wider to repressurize the adsorber vessel faster if desired. When the adsorber vessel has cooled to ambient temperature, flow of the cooling water is halted and the bed is ready for reuse to dehydrate ethanol.

During the entire desorption cycle compressor 60 has been operated only when needed. Although the vacuum may be broken when cooling of the bed begins, flow of gas through the bed should be minimized since desiccant bed would adsorb water from the gas.

Once cooled below about 150° F. adsorber vessel 30 is ready for service. In the regeneration cycle mode illustrated by FIG. 3, an 8-hour cycle time includes cooling to about 100° F. before time comes to take vessel 40 out of adsorption cycle service, and reuse freshly regenerated vessel 20 for adsorption purposes.

Figure 6:
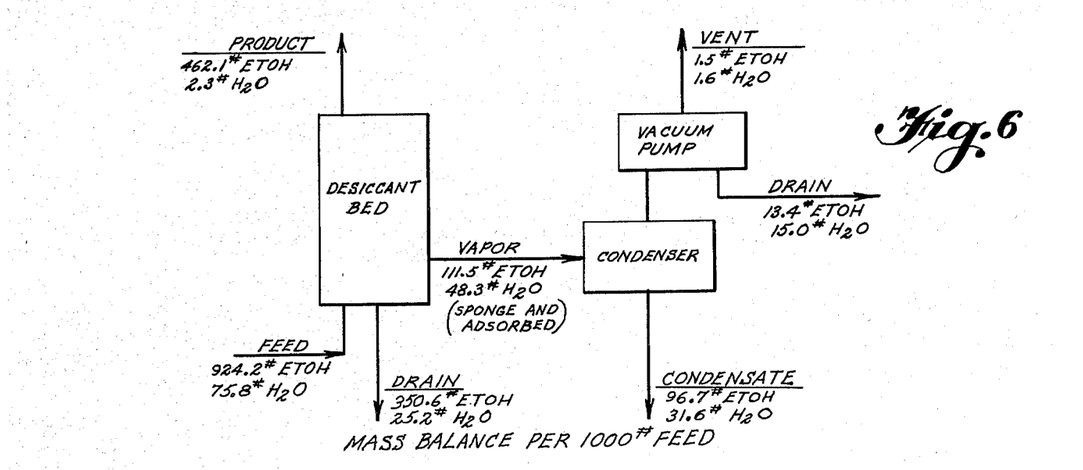
FIG. 6 is a block diagram illustrating the mass balance of the example herein.

Since the above description of how a preferred mode of this system operates may not make clear the material balance relationships present in practice of this invention, the mass balance for a pilot plant embodiment of this invention is illustrated by block diagram in FIG. 6.

The system contained 375 lbs. of desiccant per bed, operated on an 8-hour adsorption cycle time at a flow rate of 125 lbs of 190 proof ethanol per hour to handle 1000 lbs of 190 proof ethanol per cycle. As illustrated on FIG. 6, 924.2 lbs of ethanol and 75.3 lbs of water enters the system per adsorption cycle. A steam coil in the desiccant bed heated with 150 psig steam applies about 2310 BTU per gallon of 199+ proof ethanol product during the ambient pressure heating phase of the regeneration. A liquid ring two-stage vacuum air ejector pump powered by a 25 hp motor capable of evacuating to 10 torr is turned on after 2½ hours of ambient pressure regeneration. The vacuum and continued steam heating is applied to the bed for two hours, followed by cooling the bed by substituting 100° F. water for the steam in the heat exchange coils for the remainder of the regeneration cycle. The energy required for the vacuum and steam heating portion of the regeneration cycle is about 395 BTU per gallon of 199+ product.

Certain noteworthy characteristics of the ethanol dehydration system of this invention can be seen from the mass balance of FIG. 6.

At a flow rate of 125 lbs/hr. the first four hours of the eight hour adsorption cycle is required to fill the desiccant bed and containment vessel with the liquid ethanol. Effective dehydration of the ethanol then takes place for the remaining four hours, which explains why only about 465 pounds of 199+ proof ethanol product is produced per adsorption cycle.

Just over 375 lbs. of liquid may be drained from the bed, and in the mode herein exemplified 20 psia of nitrogen applied to the bed from above forces out the about 375 lbs. of ethanol and water from the adsorption vessel. The drain effluent is in part, interstitial feed material i.e., about 75%, but in part is partially dehydrated ethanol i.e., about 25%. In total, the drain liquid is about 191 proof ethanol. In passing, it is noted that downflow adsorption flow of 190 proof ethanol through the adsorber may be employed and is herein contemplated, but not as a preferred embodiment.

The quantity of absorbed and adsorbed water and ethanol to be vaporized amounts to about 40% of dry bed weight, and in this example, is nearly 160 lbs. per cycle and per 1000 lbs. of feed. Such a substantial volume of high alcohol content vapors elutriated from the desiccant justify recovery of the ethanol therefrom. Most of the ethanol is, however, present in the 128 lbs. of vapor condensate from knockout drum 90. A relatively small volume of ethanol containing condensate may be recovered in the 28 lbs. estimated as recoverable downstream of the vacuum pump with only 3 lbs. of vapors vented (or recovered from the vent gases).

The volumes of $N_2$ used for sweep purpose in the above described exemplary modes are not known, since the sweep gas flow used during regeneration under vacuum is generated largely by pressure changes associated with the regeneration cycle and leaks in the system. As was pointed out above, draining of liquid from the adsorber is assisted by flow of $N_2$ at about 20 psia through the adsorber, which flow of gas was halted altogether when the valving shifted (i.e., valve 18 or 19 closed, valve 55 or 57 opened) to connect adsorber 20 or 40 to condenser 80, which reduced the pressure to ambient pressure. The pressure inside the adsorber throughout the principal regeneration remained at about ambient pressure. Then when vacuum pump 70 turned on, the suction drew $N_2$ from line 54, generating a sub-atmospheric pressure gas sweep through the adsorbent bed. In practice, valve 101 may be left cracked so that a small $N_2$ flow passes through the adsorbent bed throughout the regeneration cycle.

The invention herein has been described above in terms of preferred practices and modes thereof, but the invention herein is not so limited. For example, a three adsorber vessel system may be employed so that dehydration of ethanol might be more nearly continuous, with one adsorber delivering 199 proof ethanol while the second adsorber is filling (desirably with drain liquid from a previous adsorber cycle) and the third is undergoing regeneration. Another varient herein contemplated is to pass the vent gases through a freshly regenerated adsorber bed to recover the ethanol content thereof.

We claim:

1. A process for dehydrating ethanol to more than 199 proof which comprises:
    passing liquid phase ethanol through a desiccant bed adapted to dehydrate 190 proof ethanol to more than 199 proof ethanol until said desiccant bed is substantially fully saturated with adsorbed water and regenerating the desiccant bed for renewed adsorption use according to the following procedure:

heating the bed by indirect heat exchange to above about 212° F. to thereby vaporize absorbed and adsorbed ethanol and water from the bed thereafter;

applying sub-atmospheric pressures to the heated bed, desorbing in vapor phase thereby substantial additional proportions of liquid from the bed, and then cooling the bed by indirect heat exchange to temperature levels suited to adsorption service and releasing the sub-atmospheric pressures thereon.

2. The process of claim 1 including applying an inert gas sweep at about atmospheric pressure levels just prior to regeneration to drain liquid phase ethanol from the bed.

3. The process of claim 1 wherein the maximum regeneration temperature is in the range of 325° F.–375° F.

4. In a process for dehydration of ethanol from an ethanol-water mixture by alternatively adsorbing the water from liquid phase ethanol-water stream in one of at least two adsorbent beds arranged for alternatively shifting between cycles of adsorption and desorption, the improvement which comprises regenerating the adsorbent bed by desorbing absorbed and adsorbed water and ethanol by vaporizing same at temperatures exceeding 212° F. through indirect heat exchange from a heating means in the adsorbent bed, and thereafter subjecting the adsorbent bed to sub-atmospheric pressures during final stages of the regeneration thereby sweeping volatilized vapors from the bed, followed by cooling the adsorbent bed by indirect heat exchange with cooling means disposed inside the adsorbent bed.

5. The process of claim 4 which further comprises passing a stream of inert sweep gas through the adsorbent bed during the sub-atmospheric final stages.

6. The process of claim 4 including condensing the desorbed vapors at from 35°–100° F. to thereby recover the desorbed ethanol.

7. An ethanol dehydration system which comprises an adsorber unit made up of at least two adsorber vessels that alternatively operate through cycles of adsorption and desorption;

each adsorber vessel containing therein a bed of particulate adsorbent and heat exchange means inside said bed adapted to heat and to cool said bed;

means for passing liquid phase ethanol through an adsorber vessel of said adsorber unit during an adsorption cycle to adsorb the water content of the ethanol onto the particulate adsorbent therein;

means for connecting into the hereinafter defined sub-atmospheric pressure inert sweep gas loop an adsorber vessel of said adsorption unit during only the final stages of a desorption cycle to remove vapors evolved from the adsorbent bed therein being regenerated;

means for passing a heating fluid through the heat exchange means in an adsorber vessel from the beginning of the desorption cycle until liquid previously absorbed and adsorbed by the adsorbent bed has been volatilized therefrom thereby regenerating the bed;

a condenser connected to the adsorber vessel undergoing desorption to which the volatilized vapors pass;

means for passing a cooling fluid through the heat exchange means in an adsorber vessel after regeneration of the bed has been completed;

a sub-atmospheric pressure gas loop for inert sweep gas including one of said adsorber vessels, said condenser, a liquid removing means to remove condensate and a compressor, said gas loop serving to circulate sweep gas from the adsorption unit in the final stages of a desorption cycle successively through condenser, liquid removing means, and compressor, then back to the adsorption unit.

8. The ethanol dehydration of claim 7 including vacuum pump means disposed in the gas loop between said condenser and compressor adapted to be introduced selectively into the gas loop to apply sub-atmospheric pressures to the adsorber bed undergoing the final stages of the desorption cycle.

* * * * *